(12) United States Patent
Iwabuchi

(10) Patent No.: US 6,360,124 B1
(45) Date of Patent: Mar. 19, 2002

(54) HANDHELD BIOELECTRIC IMPEDANCE MEASURING APPARATUS

(75) Inventor: Tamotsu Iwabuchi, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/510,231

(22) Filed: Feb. 22, 2000

(30) Foreign Application Priority Data

Feb. 22, 1999 (JP) .......................................... 11-043379

(51) Int. Cl.[7] .............................................. A61B 5/05
(52) U.S. Cl. ..................................................... 600/547
(58) Field of Search ................................. 600/547, 493, 600/300, 504, 506, 502, 500; D24/165

(56) References Cited

U.S. PATENT DOCUMENTS

| | | | |
|---|---|---|---|
| 4,320,767 A | * 3/1982 | Villa-Real | .................... 600/493 |
| 4,949,727 A | 8/1990 | Yamazaki et al. | |
| 5,579,782 A | 12/1996 | Masuo | |
| 5,817,031 A | * 10/1998 | Masuo et al. | ................ 600/547 |

FOREIGN PATENT DOCUMENTS

| | | |
|---|---|---|
| DE | 196 23 149 C1 | 1/1998 |
| EP | 0 926 488 A2 | 6/1999 |
| JP | 11-19059 | 4/1997 |
| JP | 10-174679 | 6/1998 |
| TW | 89102346 | 10/1998 |

OTHER PUBLICATIONS

Japanese Office Action (English Translation).

* cited by examiner

Primary Examiner—John P. Lacyk
Assistant Examiner—Brian Szmal
(74) Attorney, Agent, or Firm—McDermott, Will & Emery

(57) ABSTRACT

The present invention provides a handheld bioelectric impedance measuring apparatus in which four electrodes are arranged apart with one another on both end sides of an upper and a lower side surfaces of a main body respectively, and a display section and an operation section are arranged on a front surface of the main body, so that the finger of the left hand and that of the right hand may be prevented from coming into contact with each other to improve an accuracy of the measurement as well as a convenience in operation. In addition, the present invention provides another handheld bioelectric impedance measuring apparatus in which electrodes are mounted on outer surfaces of four switches arranged apart with one another on both end sides of an upper and a lower side surfaces of a main body respectively, and a display section and an operation section are arranged on a front surface of the main body, and a power supply means is also mounted thereon for supplying said measuring apparatus with an electric power when all of said switches are in ON, independently of power switch being in OFF, and thereby for measuring the body fat rate, so that the finger of the left hand and that of the right hand may be prevented from coming into contact with each other as well as a contact pressure onto the electrodes may be secured to improve an accuracy of the measurement, and the bioelectric impedance may be measured only by gripping the electrodes to improve a convenience in operation.

9 Claims, 7 Drawing Sheets

HANDHELD BIOELECTRIC IMPEDANCE MEASURING APPARATUS

BACKGROUND OF THE INVENTION

1. Field of the Invention

The present invention generally relates to a body fat measuring device (hereafter, referred to as body fat meter), and, more particularly, to a handheld type body fat meter for determining a body fat rate based on an electric impedance measured by the use of four electrodes.

2. Description of the Prior Art

As for a conventional card type body fat meter, there is disclosed a Japanese Utility Model Publication No. Hei. 5-2164, in which said body fat meter has a display and an operation sections arranged on a front surface thereof and electrodes for measurement arranged on a back surface thereof. Though there are four measuring electrodes, they are configured so that two of said four electrodes are brought into contact with one finger of the left hand and other two are brought into contact with one finger of the right hand.

There is also provided a body fat meter of pocket game machine type by NAMCO Ltd., which has two electrodes each being disposed on each side of a main body thereof.

Furthermore, as a card type body fat meter, there are provided "PokeNAVI" and "PokeMINI" by Yamato Scale Co. Ltd., whose electrodes are arranged on a front and a back surfaces of the left and the right upper corners of a main body thereof respectively.

In the body fat meter disclosed by said Japanese Utility Model Publication No. Hei. 5-2164, the main body thereof shall be turned over when the fingers are brought into contact with the electrodes to measure the body fat rate and then shall be turned over again after measurement, which makes an operation thereof inconvenient. In addition, though there are four measuring electrodes arranged on the back surface, since two of them are brought into contact with one figure of the left hand and other two with one figure of the right hand respectively, a distance between electrodes is short and thereby it is difficult to improve an accuracy of the measurement.

As for the body fat meter provided by NAMCO Ltd., it is also difficult, similar to that described in said Publication, to improve an accuracy of the measurement. In addition, since a device thereof has a size to be enveloped by one hand, some of figures of the left and the right hands are likely to come in contact with each other during measurement, which makes a significant error.

Furthermore, in the body fat meter provided by Yamato Scale Co. Ltd., when an operation switch is operated after the electrodes being gripped, an angle between adjacent fingers should be made wider and a holding manner of the main body should be changed, which makes an operation thereof inconvenient.

An object of this invention is to provide a handheld bioelectric impedance measuring apparatus which can eliminate the aforementioned drawbacks and disadvantages of the conventional body fat meters.

SUMMARY OF THE INVENTION

The present invention provides a handheld bioelectric impedance measuring apparatus in which four electrodes are arranged apart with one another on both end sides of an upper and a lower side surfaces of a main body respectively, and a display section and an operation section are arranged on a front surface of the main body, so that the finger of the left hand and that of the right hand may be prevented from coming into contact with each other to improve an accuracy of the measurement as well as a convenience in operation. In addition, the present invention provides another handheld bioelectric impedance measuring apparatus in which electrodes are mounted on outer surfaces of four switches arranged apart with one another on both end sides of an upper and a lower side surfaces of a main body respectively, and a display section and an operation section are arranged on a front surface of the main body, and a power supply means is also mounted thereon for supplying said measuring apparatus with an electric power when all of said switches are in ON, independently of power switch being in OFF, and thereby for measuring the bioelectric impedance, so that the finger of the left hand and that of the right hand may be prevented from coming into contact with each other as well as a contact pressure onto the electrodes may be secured to improve an accuracy of the measurement, and the bioelectric impedannce may be measured only by gripping the electrodes to improve a convenience in operation.

A handheld bioelectric impedance measuring apparatus according to the present invention comprises a main body with insulating property having a card-shaped outline, four electrodes arranged apart with one another on an upper and a lower side surfaces of said main body respectively, a display section arranged on a front surface of said main body, and an operation section arranged on the front surface of said main body.

When said operation section is arranged in a lower side of said display section, numerical values of a height and a weight may be easily input by thumbs of the left and the right hands in the same manner as of a game machine, and the thumbs may be easily moved from the operation section to the electrodes on the lower side surface to measure the body fat rate because of a short distance therebetween, which provides an improved operability.

When said operation section is divided and arranged on both sides of said display section, the thumbs of the left and the right hands may be moved smoothly without any strain when the main body is gripped from both sides by both hands to operate it, which provides an improved operability.

Another handheld bioelectric impedannce measuring apparatus according to the present invention comprises a main body with insulating property having a card-shaped outline, four switches arranged apart with one another on an upper and a lower side surfaces of said main body respectively, electrodes mounted on outer surfaces of said switches, a display section arranged on a front surface of said main body, an operation section arranged on the front surface of said main body, and a control section for calculating a bioelectric impedance based on a measured result from said electrodes when all of said switches are in ON and for displaying a calculated result on said display section, so that a finger of the left hand and that of the right hand may be prevented from coming into contact with each other as well as a contact pressure onto said electrodes may be secured, and thereby an accuracy of measurement may be improved.

When an electric power source switch for supplying the measuring apparatus described above with electricity is mounted on the main body thereof and an electric power source supply means is also provided thereto which supplies said measuring apparatus with electricity when all of said switches are in ON, independently of said electric power source switch being in OFF, and allows to measure the bioelectric impedance, so that the bioelectric impedance may be measure only by gripping the electrodes, an operability may be sufficiently improved.

Furthermore, this invention also provides a handheld type body fat meter, a handheld type sphygmomanometer and a pulse rate meter which utilize a bioelectric impedance measuring apparatus as mentioned above.

This invention will now be described in further detail with regard to preferred embodiments as illustrated in the accompanying drawings.

DESCRIPTION OF THE PREFERRED EMBODIMENTS OF THE INVENTION

Figure 1:
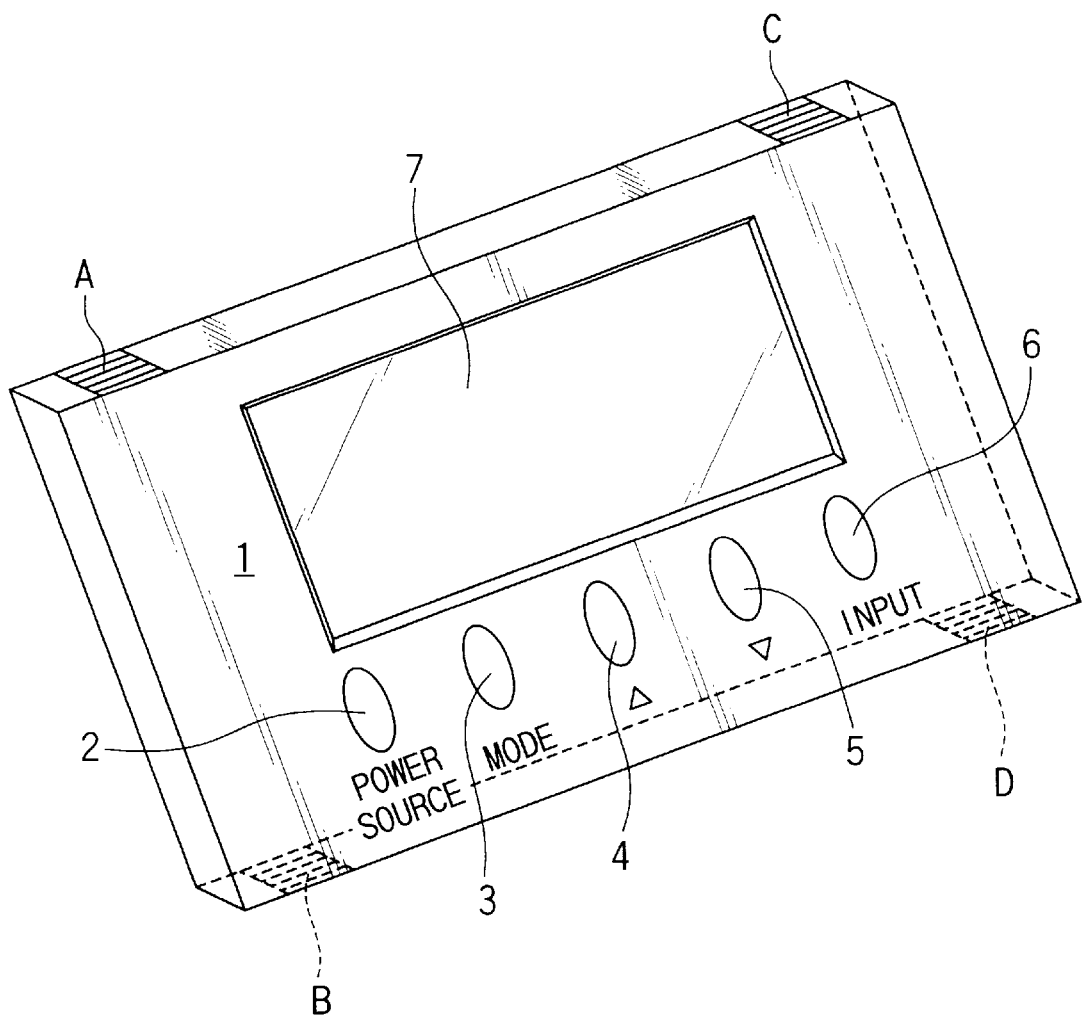
FIG. 1 is a schematic perspective view of the first embodiment of a handheld type body fat meter in accordance with the present invention.
Figure 2:
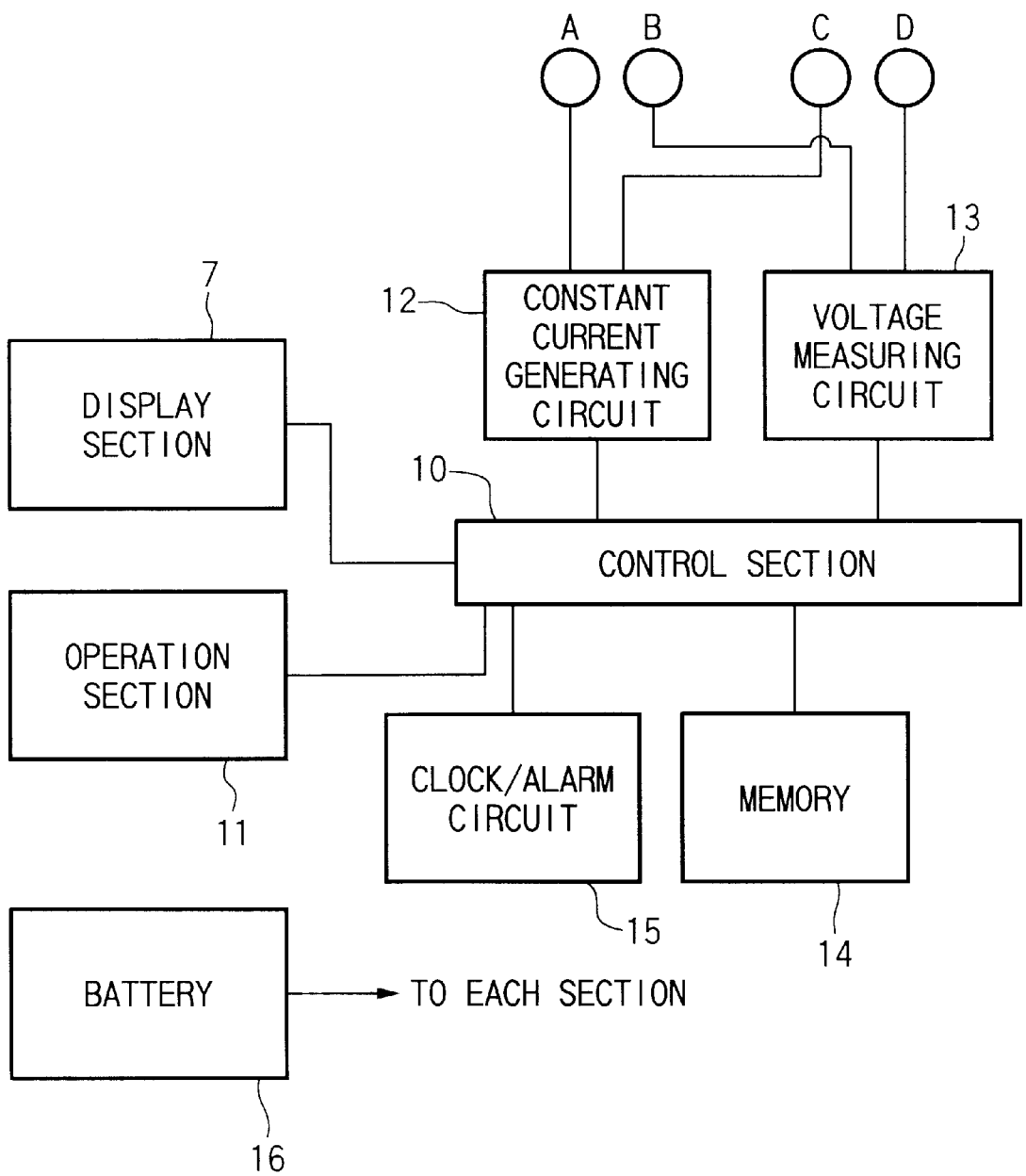
FIG. 2 is a block diagram illustrating an electric circuit of the handheld type body fat meter shown in FIG. 1.
Figure 3:
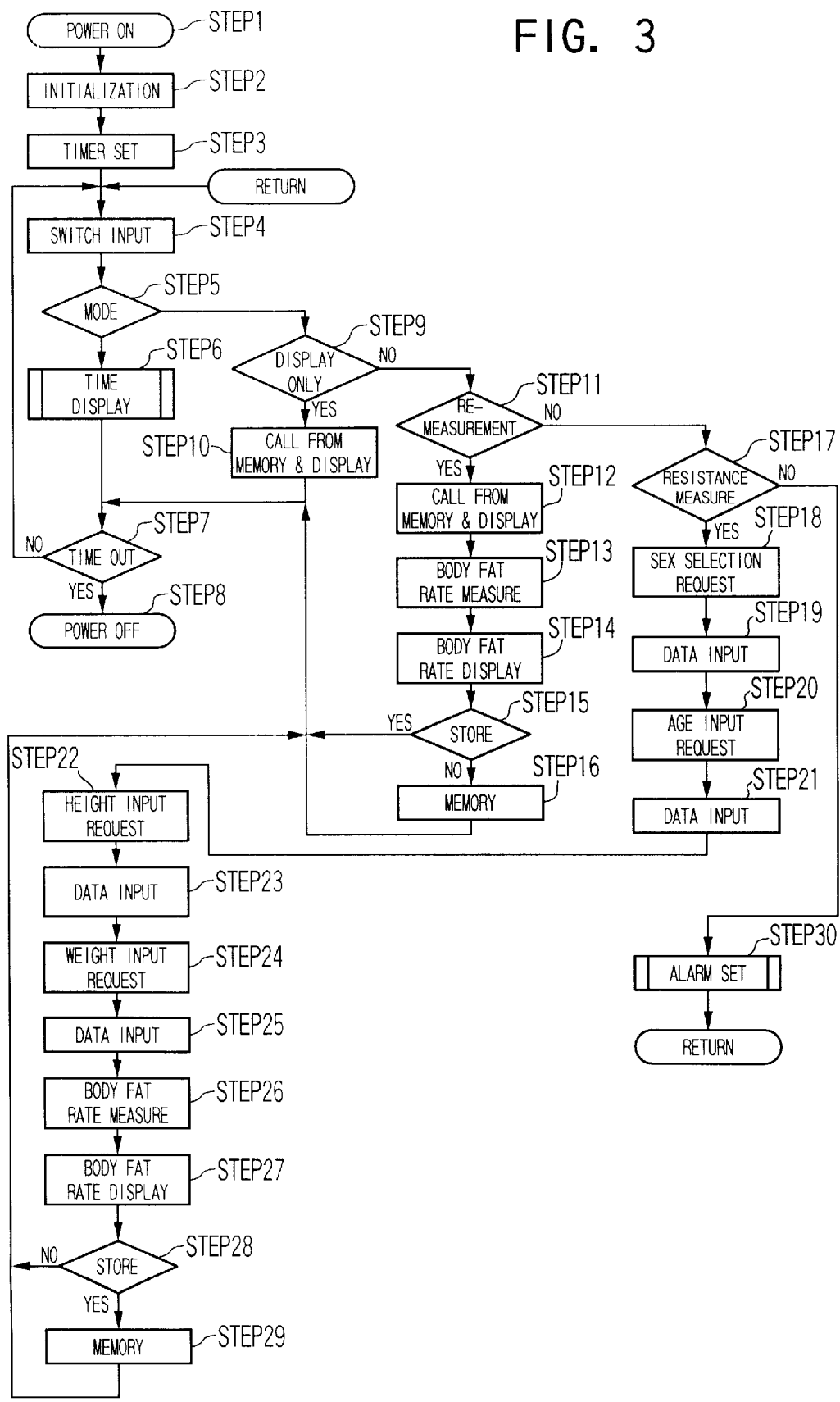
FIG. 3 illustrates a flow chart of the handheld type body fat meter shown in FIG. 1.

FIGS. 1 to 3 illustrate a first embodiment of the invention. In FIG. 1, an electric power source switch 2 for supplying electricity to a body fat meter is mounted on a left lower portion of a front surface of a main body 1 of a handheld type body fat meter, wherein said electric power source switch 2 is configured so that when said power source switch 2 is pushed once, the electricity is supplied and, when the power source switch 2 is pushed once again, the electricity is cut off. A mode switch 3, an up-switch 4, a down-switch 5 and an input switch 6 are arranged in line in this order on the right side of said power source switch 2.

Said mode switch 3 is configured so that a function of the body fat meter is changed in series every time when said mode switch 3 is pushed, starting from a display mode for displaying a data having been stored, through a re-measurement mode for measuring the body fat rate again using the data having been stored, and a new measurement mode for newly measuring the body fat rate, to an alarm set mode for setting an alarm time for measuring the body fat rate at a fixed time everyday.

The up-switch 4 increases a value of a displayed data when pushed repeatedly or continuously under the new measurement mode, the alarm set mode or the like. The down-switch 5 decreases a value of the displayed data having been increased by the up-switch 4. The input switch 6 sends the displayed data set by the up-switch 4 and the down-switch 5 under each of said modes as a confirmed data to a control section 10 and/or a memory 14 of FIG. 2. A display section 7 for displaying a data set and input by said switches, a measured result, a guidance message for the measurement or the like is provided on an upper portion of the front surface of the main body 1.

An electrode "A" made of conductive metal chip or metal-plated material is provided near to a left end portion of an upper surface of the main body 1, and an electrode "C" made of the same material as of the electrode "A" is provided near to a right end portion of the upper surface. Though forefingers of the left and the right hands are typically brought into contact with said electrodes "A" and "C" respectively, a middle finger, a medical finger or a little finger may be used instead and said electrodes "A" and "C" are arranged placing a certain distance therebetween so that the finger of the left hand and that of the right hand may not come in contact with each other. Electrodes "B" and "D" are provided on a lower side surface of the main body 1 as the electrodes "A" and "C" are on the upper surface. Thumbs of the left and the right hands are brought into contact with said electrodes "B" and "D" respectively.

FIG. 2 illustrates an electric circuit of the handheld type body fat meter shown in FIG. 1. The control section 10 processes a data sent from an operation section 11 comprising a group of switches including the mode switch 3, the up-switch 4, the down-switch 5 or the like, and displays a calculated data on a display section 7. A constant-current generating circuit 12 for supplying a constant current to the electrodes "A" and "C" is connected to said control section 10, and a voltage measuring circuit 13 for measuring voltages of the electrodes "B" and "D" is also connected to the control section 10. In addition, a memory 14 for storing a data such as an input data from the operation section 11, a data of calculated result or the like is connected to the control section 10. Further, a well-known clock/alarm circuit 15 for displaying a time or an alarm time on the display section 7 is also connected to the control section 10.

A battery 16 supplies electricity to respective sections when the electric power switch 2 is pushed once and cuts off the supply when the power switch 2 is pushed again.

FIG. 3 is a flow chart illustrating an operation of the first embodiment. Though this flow chart includes something different from an actual one because it illustrates an outline of the concept of various processings, the operation of the body fat meter will be described with reference to this flow chart. When the electric power source switch 2 shown in FIG. 1 is turned on, the electricity is supplied to each circuit, the control section or the like shown in FIG. 2 (step 1), and then the display section, each circuit or the like are initialized at step 2. Then a timer is set at step 3. The timer leads this system to time-out at step 7 when the system is left without any operation by said switches for predetermined time period, for example 5 minutes, and cuts off the power source at step 8 to prevent a consumption of the battery during being left.

On/off data from said switches are sent to the control section 10 at step 4, and then the process moves to step 5. Though the step 5 is placed to judge an input of the mode switch 3, the process moves to step 6 because the mode switch 3 has not been turned on just after the power source switch was turned on, and displays a current time on the display section 7 based on the time data from the clock/alarm circuit 15. Since the well-known technology is employed in time display, the description thereof will be omitted in this embodiment. The process judges "No" at step 7 as long as said predetermined time period has not passed, and returns to step 4 to display the current time continuously and to repeat an operation to wait for the input from switches.

Under the waiting condition for the input from the switches as described above, when the mode switch 3 is turned on, the process moves from step 5 to the display mode of steps 9 and 10. Thus, when the mode switch 3 is pushed once, the current time display is cancelled and, at step 10, the data of sex, age, height, weight and body fat rate which were input and measured in the past are called out from the memory 14 and are displayed on the display section 7. This display is continuously held until the process goes into the time-out in step 7 or the mode switch 3 is pushed again.

Under this display mode condition, when the mode switch 3 is pushed once, the process judges to be "No" at step 9 and moves to the re-measurement mode of step 11. In the re-measurement mode, the display in the display mode is cancelled and, at step 12, the data of sex, age, height, weight which are stored in the memory 14 are called and displayed on the display section 7 and at the same time the message indicating the measuring of the body fat rate based on these data is displayed on the display section 7. At step 13, the constant current is applied between the forefingers of the left and the right hands of the user to be measured from the constant current generating circuit 12 shown in FIG. 2 through the electrodes "A", "C", and the voltage between the thumbs of the left and the right hands of the user is measured by the voltage measuring circuit 13 through the electrodes "B", "D", and then the electric impedance between the thumbs of the user is measured based on the formula: Resistance=Voltage/Current. The body fat rate is calculated based on this electric impedance and the data which have been called out and displayed on the display section 7 previously, and this calculated result is displayed on the display section together with the data having been displayed thereon previously (step 14). At the end of this displaying, whether the data of displayed result shall be stored in the memory 14 for use in case of the display mode being selected in the future is judged by pushing the input switch 6, and, if not, the process moves to step 7 and, if yes, it moves to step 16 to store the result data into the memory 14 and then moves to step 7.

Under this displaying condition above, when the mode switch 3 is pushed again, the process judges to be "No" at step 11 and cancels the display of step 14 to move to the new measurement mode of steps 17 to 29. At step 18, the sex of the user is selected by displaying both sexes on the display section 7 and by pushing the up-switch 4 or the down-switch 5 to select one, and then this data is confirmed by pushing the input switch 6 (step 19), and, at step 20, a message requesting to input the age data of the user is displayed. In this display for inputting the age data, an initial numerical value of the age to be input, for example, 20 years old, is displayed adding to said message, and is modified to the user's age by increasing or decreasing said displayed numerical value by pushing the up-switch 4 or down-switch 5 repeatedly or continuously.

This data is confirmed by pushing the input switch 6 (step 21), and, at step 22, a message requesting to input the height data of the user is displayed. In the subsequent steps 23 to 25, the height and the weight data of the user are input by the use of the up-switch 4 and the down-switch 5 and then these data are confirmed by the input switch 6 in the same manner as of the steps 20, 21. Since the processes between steps 26 and 29 is the same as those between steps 13 and 16, the description thereof will be omitted. In this new measurement mode, the displaying condition of step 27 is held eventually.

Under this displaying condition above, when the mode switch 3 is pushed again, the process judges to be "No" at step 17 and cancels the display of step 27 to moves to the alarm set mode of step 30. Since this alarm set mode has the same process with that of the well-known alarm set processing of the dock, the description thereof will be omitted. When the alarm set is completed, the process returns to step 4 to repeat the processing between steps 4 and 7, and displays the current time. When the mode switch is pushed plural times successively, the process directly jumps to one of the modes shown in FIG. 3 depending on the times of pushing.

In this embodiment, when the mode switch is pushed three times, the mode moves to the alarm set mode, and, when the mode switch is pushed four times, it returns to the current time display mode, and, when the mode switch is pushed five times or more, the mode is moved forward in order. In any steps shown in FIG. 3, when the electric power source switch 2 is pushed again, the electric supply is cut off and the power source is turned off.

Figure 4:
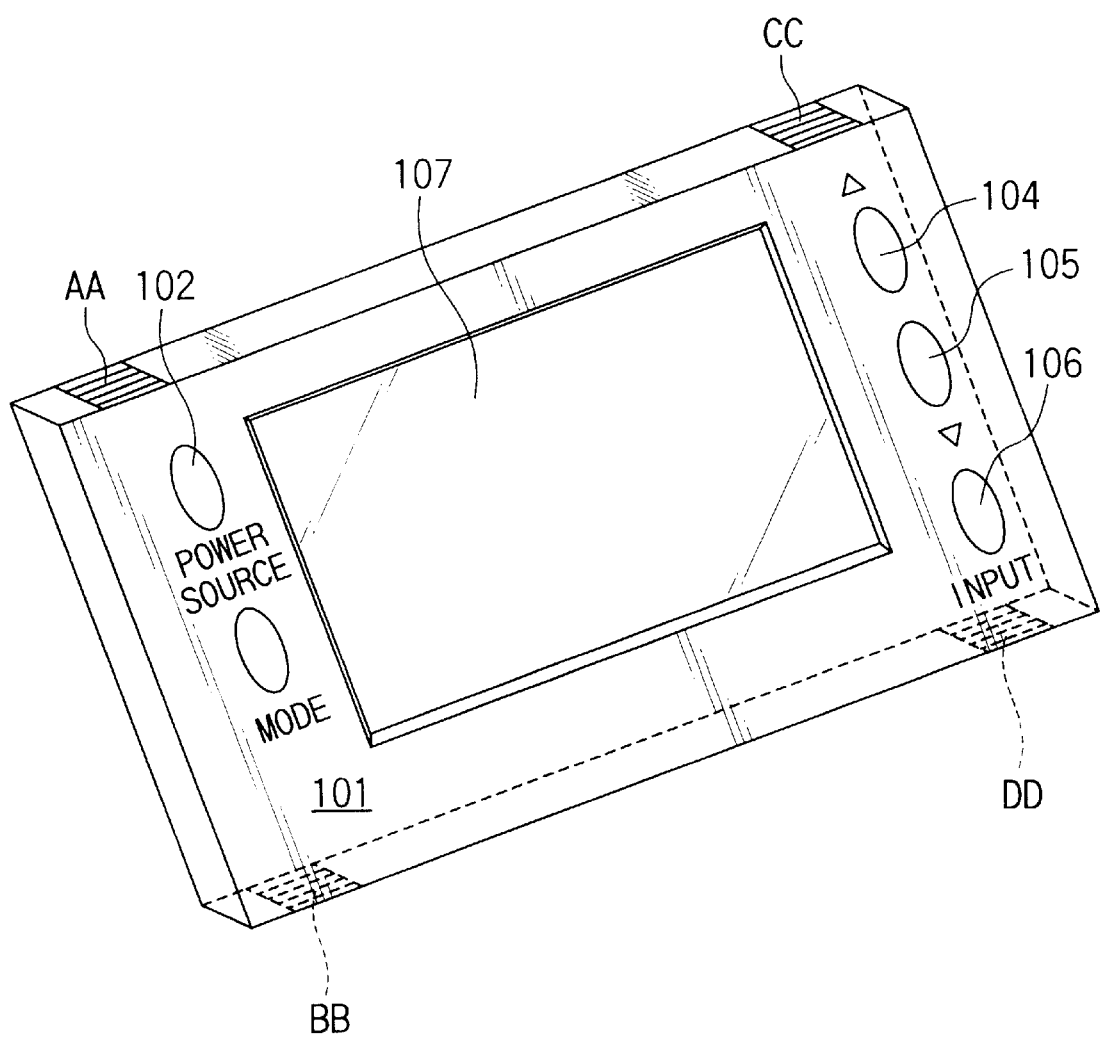
FIG. 4 is a schematic perspective view of the second embodiment of the handheld type body fat meter in accordance with the present invention.

FIG. 4 shows a second embodiment of the invention, wherein an arrangement of an operation section comprising five switches including the electric power source switch 2 to the input switch 6 of the first embodiment shown in FIGS. 1 to 3 is moved from the lower side of the display section 7 to each side of the display section 7 by separating them into two parts. The reference numerals in FIG. 4 are formed by adding 100 to those in FIG. 1 respectively, and reference characters are indicated by double letters. Other parts than described above are the same with those of the first embodiment. In this arrangement, a main body 101 is gripped from both sides by each of the left and the right hands, and an electric power source switch 102 and a mode switch 103 are operated by the left thumb and an up-switch 104, a down-switch 105 and an input switch 106 are operated by the right thumb, so that a back surface of a main body can be supported by other four fingers, which allows the left and the right thumbs to move stably, naturally and without any strain and thereby provides an improved operability.

When the left and the right forefingers are brought into contact with electrodes "AA" and "CC" respectively, the left and the right little fingers are brought into contact with electrodes "BB" and "DD" respectively, the back surface of the main body is supported by the left and the right middle and medical fingers, and the switches 102 to 106 arranged separately on the left and the right sides of the front surface of the main body are operated by the left and the right thumbs, the left and the right thumbs are completely made free from the measurement of the body fat rate, which may provide more improved operability. Though two switches are arranged on the left side of the main body and three switches are on the right side in this second embodiment, the arrangement of the switches need not be limited to this pattern but may be changed within an acceptable range of operability including an increase of number of switches.

Figure 5:
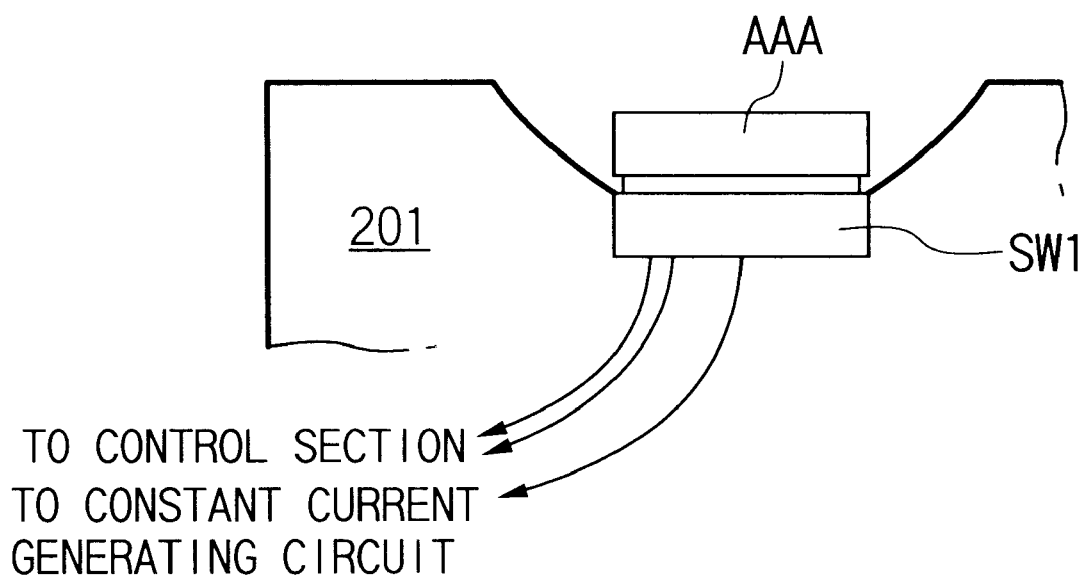
FIG. 5 illustrates a part of the third embodiment of the handheld type body fat meter in accordance with the present invention.

FIG. 5 shows a third embodiment of the invention, wherein a switch is provided on each of four electrode portions of the first and the second embodiments and an electrode is mounted on the upper surface of said switch. Other parts than described above are the same with those of the first and the second embodiments. In concrete, an upper surface of a main body 201 is recessed at its electrode portion to form a switch SW1 therein, and an electrode "AAA" which is connected to the constant current generating circuit is mounted on an upper surface of said switch SW1. The switch SW1 is provided with a lead wire for ascertaining the conduction, which is electrically connected to the control section. In this third embodiment, though not shown, other switches SW2, SW3 and SW4 and other electrodes "BBB", "CCC" and "DDD" which are similar to the switch SW1 and the electrode "AAA" are provided on the-upper and the lower side, surfaces of the main body 201 as of the first and the second embodiments. Preferably, the top surfaces of the electrodes "AAA" to "DDD" are in a level of height equal to or lower than that of the upper side surface of the main body 201 so that the switch may not be turned on by touching other materials in a bag or the like while being carried with.

Figure 6:
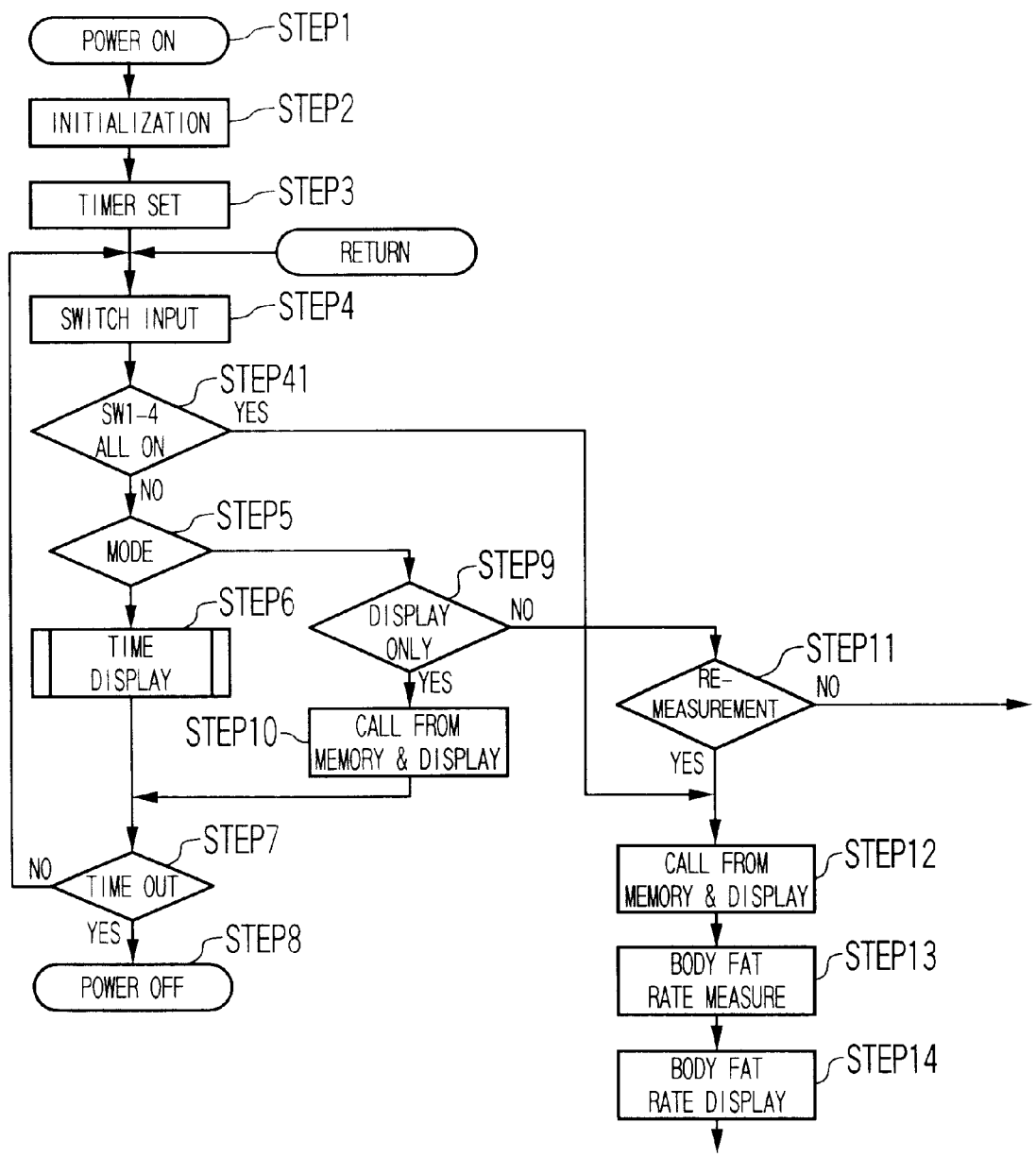
FIG. 6 illustrates a part of a flow chart of the handheld type body fat meter shown in FIG. 5.

An operation of the third embodiment will be described with reference to a flow chart of FIG. 6 which is generated by changing a part of that of FIG. 3. What is not illustrated therein is the same with the corresponding portion of the first and the second embodiments. In FIG. 6, step 41 is inserted between steps 4 and 6 so that the process may move to step 12 when all of the switches SW1 to SW4 are in ON, independently of the conditions of the switches such as mode switch or the like, to enter the re-measurement mode of the body fat rate and to measure the body fat rate based on the data having been stored and to display it. Since the handheld type body fat meter is generally utilized as a personal use, other people than a specified user is not likely to measure the body fat rate based on the specified user's data stored therein and therefore there is little problem of erroneous measuring.

Figure 7:
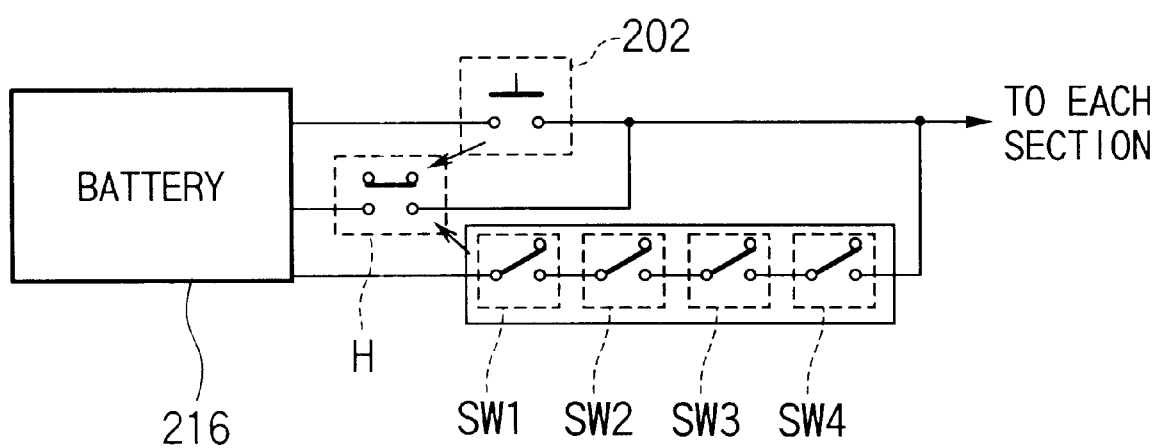
FIG. 7 illustrates a part of an electric circuit of the fourth embodiment of the handheld type body fat meter in accordance with the present invention.

FIG. 7 shows a fourth embodiment of the invention, wherein each of the switches SW1 to SW4 of the third embodiment is formed to have a switch having two contacts and each of the second contacts is connected in series between a battery 216 and each portion for which the electricity is to be supplied. As a result, by the use of a self-hold switch H which continues power supply for each portion when an electric power source switch 202 is turned on, the electricity may be supplied to each portion when all contacts of the switches SW1 to SW4 are in ON, independently of the condition of the electric power source switch 202, which allows the body fat rate to be measured in the same operation as of the third embodiment. Though the electricity is supplied by an electric power supply means comprising switches SW1 to SW4 and the self-hold switch H in this fourth embodiment, other configuration may be employed as long as the same function would be performed.

When this handheld type body fat meter is used by plural users, all the necessity is that each of the steps 9, 11 and 17 of the first and the second embodiments is followed by a step for displaying data of said plural users and a step for selecting a data among the displayed plural data by the up and/or the down-switches and for confirming it by the input switch. When the data of plural users are to be stored, steps 15 and 28 are followed by a step for selecting a user among plural users, for whom the data shall be stored.

In the third and the fourth embodiments of FIG. 6, not after step 11 but after a junction with a flow from step 41 and immediately before step 12, a step for displaying data of plural users and for inputting the data of the objective user is inserted.

Further, in the third and the fourth embodiments, the selection of the user among plural users may be performed by counting the number of times where all the switches SW1 to SW4 are in ON.

Although a handheld type body fat meter wherein a body fat rate or body fat amount is calculated from the measured bioelectric impedance has been described, it should be noted that this invention is not limited to such embodiments. For example, this invention may provide a handheld type sphygmomanometer wherein a blood pressure can be measured on the basis of a change in the bioelectric impedance measured by the above-mentioned bioelectric impedance measuring apparatus, a pulse rate meter wherein a pulse rate can be measured on the basis of a change in the bioelectric impedance measured by the abovementioned bioelectric impedance measuring apparatus, etc.

What is claimed is:

1. A handheld bioelectric impedance measuring apparatus comprising:

a main body with insulating property having a card-shaped outline;

four switches arranged apart with one another on an upper and a lower side surfaces of said main body respectively;

electrodes mounted on outer surfaces of said switches, said switches being turned on when a user grips said electrodes with each of fingers of the user's hands contacting with each of said electrodes;

a display section arranged on a front surface of said main body;

an operation section arranged on the front surface of said main body; and a control section for calculating a bioelectric impedance based on a measured result from said electrode when all of said switches are ON and for displaying a calculated result on said display section.

2. A handheld bioelectric impedance measuring apparatus in accordance with claim 1, wherein said operation section is arranged on a lower side of said display section.

3. A handheld bioelectric impedance measuring apparatus in accordance with claim 1, wherein said operation section is divided and arranged on both sides of said display section.

4. A handheld bioelectric impedance measuring apparatus in accordance with claim 1, wherein an electric power source switch for supplying said measuring apparatus with electricity is mounted on the main body thereof and an electric power source supply means is also provided thereto which supplies said measuring apparatus with electricity when all of said switches are ON, independently of said electric power source switch being OFF, and allows to measure the body fat rate.

5. A handheld bioelectric impedance measuring apparatus in accordance with claim 1 or 4, wherein said apparatus is used as a body fat meter.

6. A handheld bioelectric impedance measuring apparatus in accordance with claim 1 or 4, wherein said apparatus is used as a pulse rate meter.

7. A handheld bioelectric impedance measuring apparatus in accordance with claim 1 or 4, wherein the top surfaces of said electrodes are in a level of height equal to or lower than that of the upper side surface of said main body.

8. A handheld bioelectric impedance measuring apparatus in accordance with claim 5, wherein the top surfaces of said electrodes are in a level of height equal to or lower than that of the upper side surface of said main body.

9. A handheld bioelectric impedance measuring apparatus in accordance with claim 6, wherein the top surfaces of said electrodes are in a level of height equal to or lower than that of the upper side surface of said main body.

* * * * *